(12) United States Patent  
Connell et al.

(10) Patent No.: US 7,758,560 B2
(45) Date of Patent: Jul. 20, 2010

(54) HAZARDOUS MATERIAL HANDLING SYSTEM AND METHOD

(75) Inventors: Edward G. Connell, Grayslake, IL (US); Marwan Fathallah, Mundelein, IL (US); Kenneth A. Hsu, Highland Park, IL (US); John Norman, Gurnee, IL (US); William L. Rudzena, McHenry, IL (US); Karl J. Sprague, Waukegan, IL (US); John S. Ziegler, Arlington Heights, IL (US)

(73) Assignee: Hospira, Inc., Lake Forest, IL (US)

( * ) Notice: Subject to any disclaimer, the term of this patent is extended or adjusted under 35 U.S.C. 154(b) by 552 days.

(21) Appl. No.: 11/490,903

(22) Filed: Jul. 21, 2006

(65) Prior Publication Data

US 2006/0259004 A1  Nov. 16, 2006

Related U.S. Application Data

(62) Division of application No. 10/453,393, filed on Jun. 3, 2003, now abandoned.

(51) Int. Cl.
*A61M 5/32* (2006.01)
*A61B 19/00* (2006.01)
*B67B 7/00* (2006.01)
*G01F 11/00* (2006.01)

(52) U.S. Cl. ............... 604/414; 604/403; 604/411; 222/1

(58) Field of Classification Search .......... 604/247, 604/403, 408, 411, 414, 415
See application file for complete search history.

(56) References Cited

U.S. PATENT DOCUMENTS 3,940,003 A 2/1976 Larson 4,401,432 A 8/1983 Schwartz
4,564,054 A 1/1986 Gustavsson
4,645,073 A 2/1987 Homan
4,673,404 A 6/1987 Gustavsson (Continued)

FOREIGN PATENT DOCUMENTS

DE  1567108  2/1977

(Continued)

OTHER PUBLICATIONS

M. R. Graff, et al, "Assessment by Patients with Diabetes Mellitus of Two Insulin Pen Delivery Systems Versus a Vial and Syringe", Clinical Therapeutics, vol. 20, No. 3, 1998, pp. 486-496.
A. Kadiri, et al, "Comparison of NovoPen 3 and syringes/vials in the acceptance of insulin therapy in NIDDM patients with secondary failure to oral hypoglycaemic agents", Diabetes Research and Clinical Practice, vol. 41, 1998, pp. 15-23.

*Primary Examiner*—Melanie J Hand
(74) *Attorney, Agent, or Firm*—Michael R. Crabb

(57) ABSTRACT

A method and system for handling hazardous materials contained in a vial includes an isolation enclosure having an opening selectively sealable about the vial, a bag body portion, and a cap portion. A latching extraction element is attached to the cap portion and has a preceding engaging member to secure the vial to the isolation enclosure, an extraction member to be inserted into the vial and remove material therefrom, and a primary engaging member to secure the vial to the extraction member. A valve is mounted outside the isolation enclosure and controls the flow of fluid from the vial. An adaptor having a reseal member permits flow when coupled to the valve and restricts flow when uncoupled from the valve. Once uncoupled, the adaptor is removably associated with a second valve located remotely from the isolation enclosure, allowing fluid to pass into the second valve.

9 Claims, 9 Drawing Sheets

U.S. PATENT DOCUMENTS

| | | |
|---|---|---|
| 4,785,859 A | 11/1988 | Gustavsson |
| 5,195,980 A | 3/1993 | Catlin |
| 5,380,306 A | 1/1995 | Brinon |
| 5,403,293 A | 4/1995 | Grabenkort |
| 5,437,650 A | 8/1995 | Larkin et al. |
| 5,492,147 A | 2/1996 | Challender et al. |
| 5,509,912 A | 4/1996 | Vaillancourt et al. |
| 5,616,129 A | 4/1997 | Mayer |
| 5,820,614 A | 10/1998 | Erskine et al. |
| 5,833,674 A | 11/1998 | Turnbull et al. |
| 6,068,617 A * | 5/2000 | Richmond ............. 604/255 |
| 6,096,011 A | 8/2000 | Trombley et al. |
| 6,171,287 B1 | 1/2001 | Lynn et al. |
| 6,173,852 B1 | 1/2001 | Browne |
| 6,221,041 B1 | 4/2001 | Russo |
| 6,290,682 B1 * | 9/2001 | Myers ................. 604/247 |
| 2003/0032940 A1 | 2/2003 | Doyle |

FOREIGN PATENT DOCUMENTS

| | | |
|---|---|---|
| DE | 19938078 | 8/1999 |
| EP | 240144 A | 10/1987 |
| EP | 0273015 | 6/1988 |
| EP | 0335378 | 10/1989 |
| EP | 335378 A2 * | 10/1989 |
| EP | 544654 B1 | 6/1993 |
| FR | 2773735 | 7/1999 |
| GB | 2328432 | 2/1999 |
| JP | 02001277 | 1/1990 |
| JP | U06070737 | 10/1994 |
| WO | 98/19724 | 5/1998 |
| WO | 00/35517 | 6/2000 |

\* cited by examiner

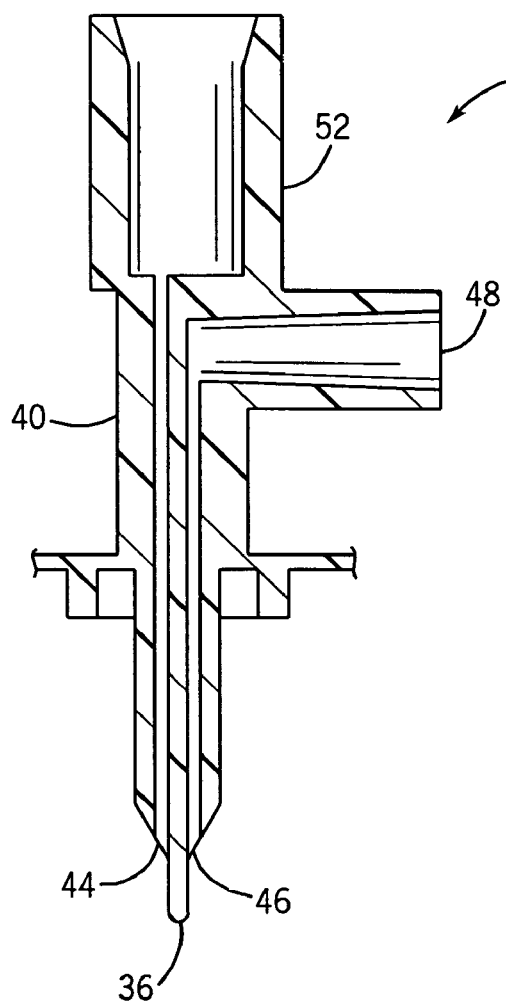
FIG. 6
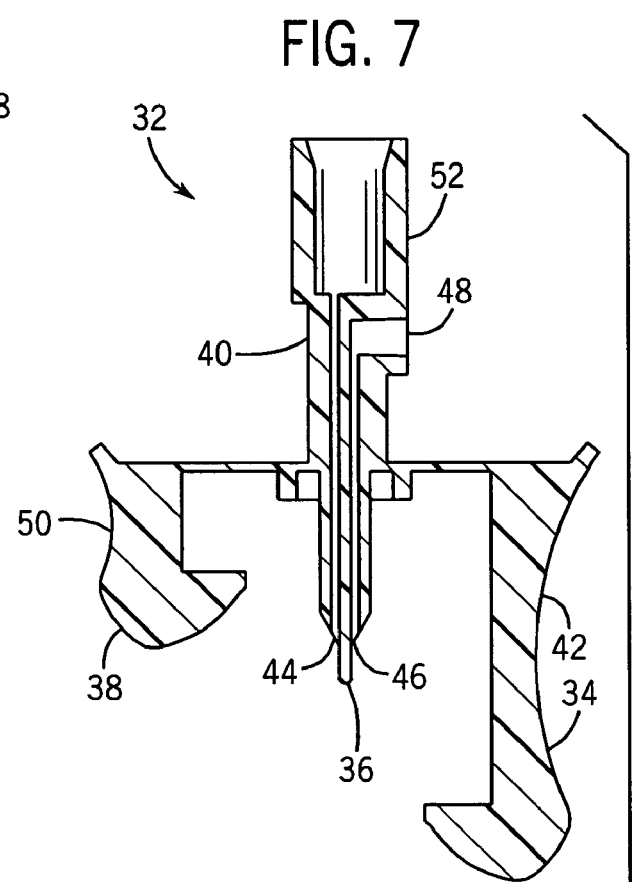
FIG. 7
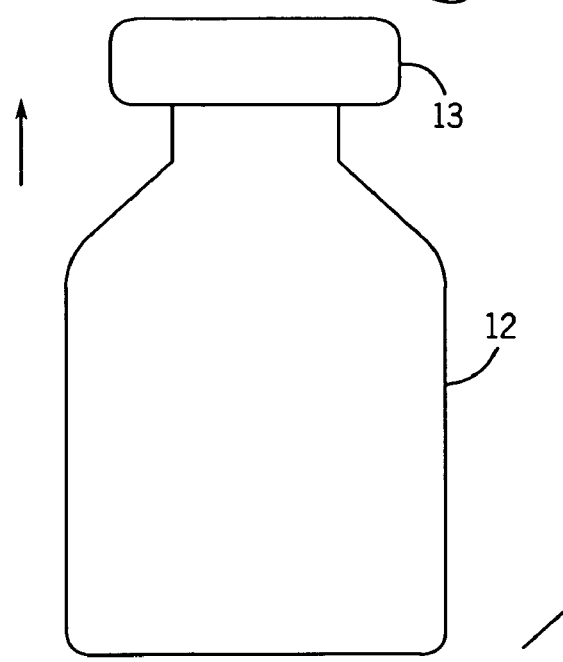

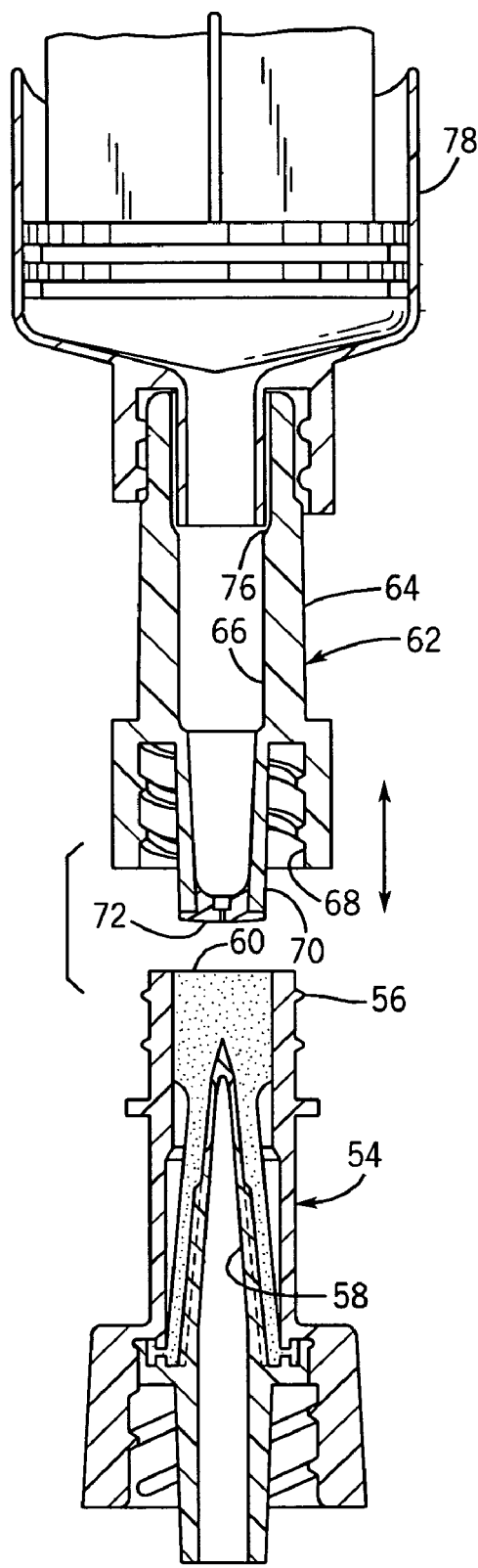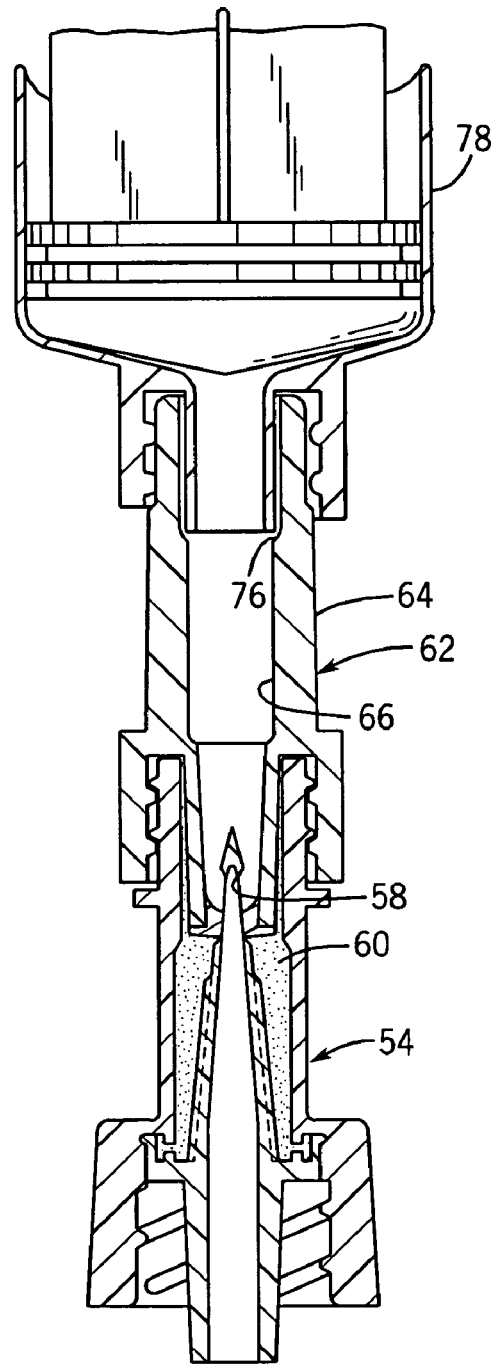
FIG. 12
FIG. 13

HAZARDOUS MATERIAL HANDLING SYSTEM AND METHOD

CROSS-REFERENCE TO RELATED APPLICATIONS

This application is a divisional of U.S. Ser. No. 10/453,393 filed Jun. 3, 2003 now abandoned.

BACKGROUND OF THE INVENTION

The present invention relates to the field of handling hazardous materials, including but not limited to materials such as drugs used for medical purposes. More particularly, this invention relates to a means and method for enabling a user to transfer a hazardous material from a sealed vial or container without allowing significant leakage of the material to the environment. Specific examples of hazardous materials to which the invention is particularly applicable include but are not limited to liquid, freeze dried or powdered cytotoxic drugs that are used extensively in chemotherapy treatment of cancer patients and radiographic materials.

High toxicity materials, including cytotoxic drugs and radiographic materials, are often enclosed in small bottles or vials that have an opening sealed by an elastomeric plug. It is highly desirable to prevent spillage or escape of even minimal amounts of hazardous materials in either liquid or gas form. Small droplets of materials could undesirably contaminate the ambient environment or come in contact with the person administering the substance.

Hazardous drugs are compounded in different ways. In large hospital pharmacies and homecare pharmacies, pharmacy technicians wearing gowns and double gloves compound hazardous drugs under vented biological laboratory hoods. These specially designed hoods are expensive and take up valuable floor space. In hospital wards, clinics, doctors' offices and other locations, laboratory hoods may not be readily available and the personnel compounding the drugs may not usually wear such elaborate protective equipment. Shelf life limitations and patient specific dosing requirements may demand that the drug be mixed closer in time and space to the point of care.

According to one conventional means and method used at the point of care, the user utilizes a sharp needle attached to a syringe to pierce and elastomeric plug or other cap that seals the vial and draw the drug out, often after injecting a suitable solvent or diluents into the vial. The user then injects the drug into a reseal element on an intravenous (IV) container from which the drug is delivered to the patient. Unfortunately, this method creates another hazard in that the person handling the drug or someone else can be "pricked" by the sharp needle.

Therefore, a principal object of this invention is to provide a method and means securing a vial within an impermeable isolation enclosure.

A further object of the invention is to provide a method and means for piercing a vial within the impermeable isolation enclosure in a fixed position; and selectively accessing the contents of the vial.

Another object of the invention is to provide a method and means for safely transferring a portion of the vial contents, while the vial remains pierced within an impermeable isolation enclosure.

These and other objects will be apparent to those skilled in the art.

SUMMARY OF THE INVENTION

A method and system for handling hazardous materials contained in a vial includes and isolation enclosure having an opening selectively sealable about the vial, a bag body portion, and a cap portion. A latching extraction element is attached to the cap portion and has a preceding engaging member to secure the vial to the isolation enclosure, an extraction member adapted to be inserted into the vial and remove material therefrom, and a primary engaging member to secure the vial to the extraction member. A valve mounted outside the isolation enclosure controls the flow or fluid from the vial. An adaptor having a reseal member permits flow when coupled to the valve and restricts flow when uncoupled from the valve. Once uncoupled, the adaptor is removable associated with a second valve located remotely form the isolation enclosure, allowing fluid to pass into the second valve.

DESCRIPTION OF THE DRAWINGS

FIG. 6 is a sectional side view of the latching extraction element of the present invention taken on line B-B of FIG. 4;

FIGS. 7, 8, and 9 are sequential sectional side views of the latching extraction element of the present invention associating with a vial taken on line A-A of FIG. 4;

FIGS. 12 and 13 are sequential sectional side views of the adaptor attached to a syringe and associating with a valve.

DESCRIPTION OF THE PREFERRED EMBODIMENT

Figure 1:
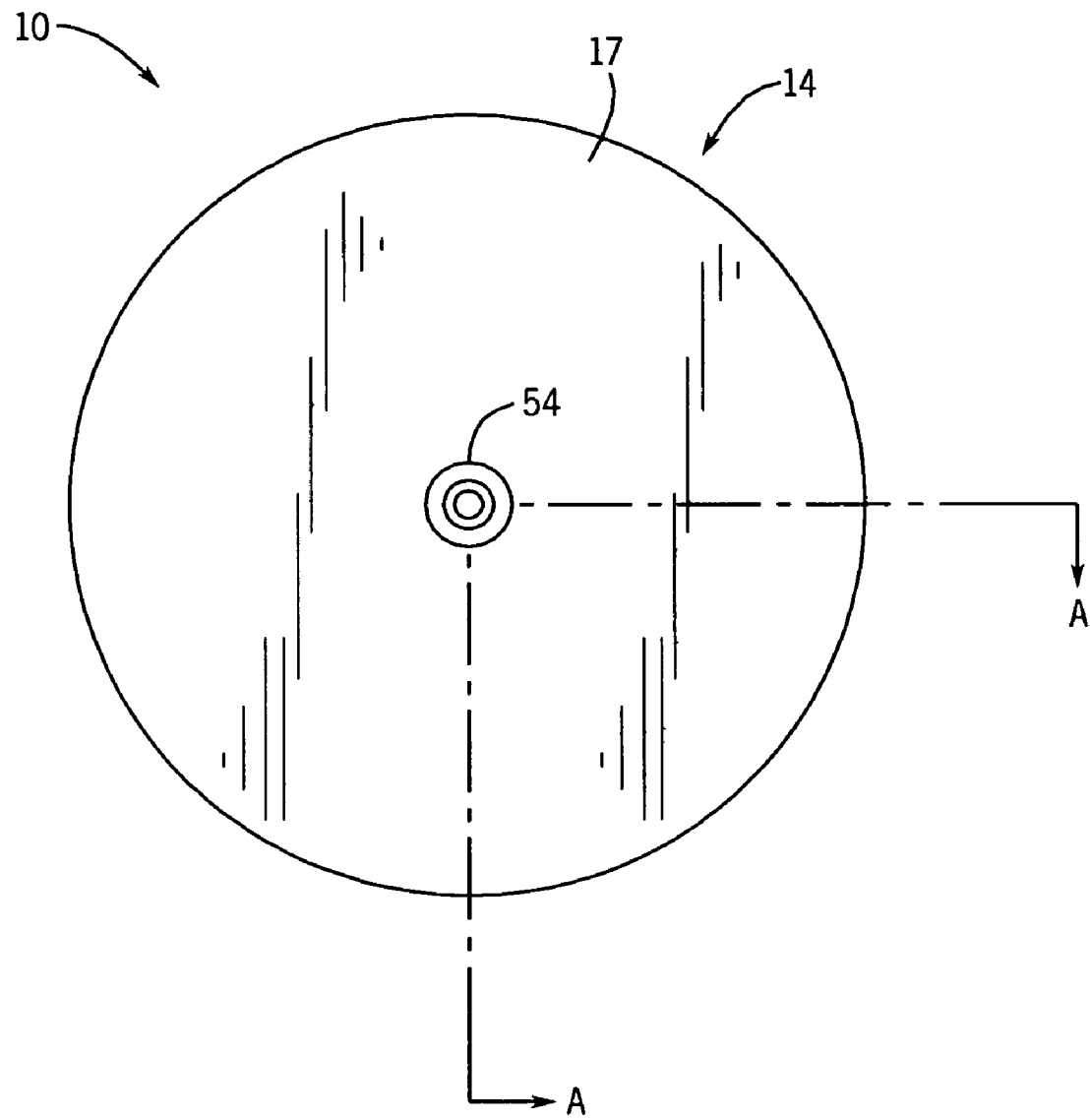
FIG. 1 is a top view of the material handling system of this invention.
Figure 2:
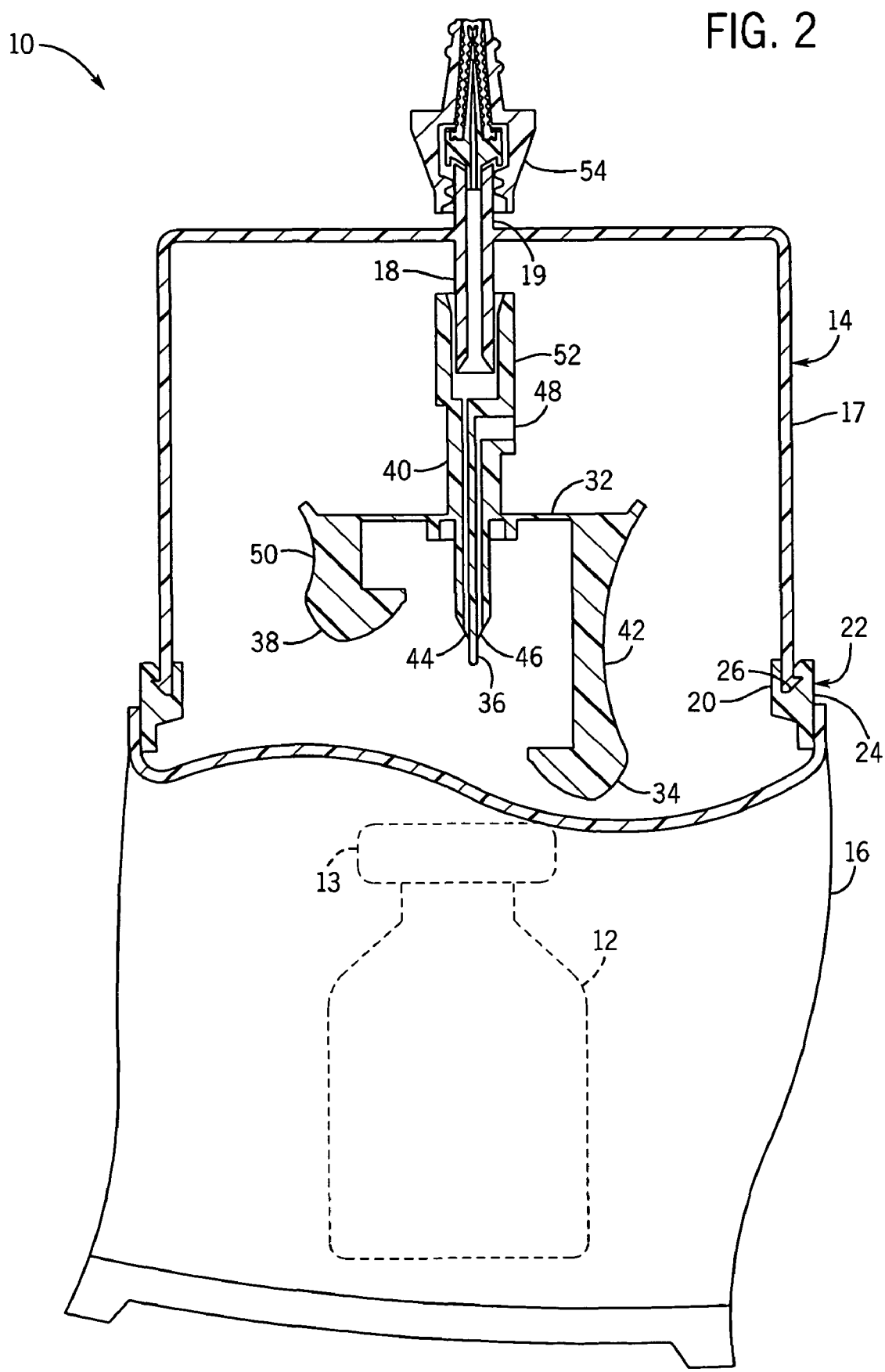
FIG. 2 is a partial sectional side view of the material handling system of this invention taken on line A-A of FIG. 1.

With reference to FIG. 2, a material handling system 10 for use with a sealed vial 12 includes an isolation enclosure 14 adapted to completely enclose the vial 12. It will be understood by those skilled in the art, that the term vial, as used herein, includes but is not limited to any type of sealed container, ampule, or bottle. A sealing closure 13 is attached to or integrally formed with the vial 12. In the case of a bottle, and elastomeric stopper can seal the opening of the container.

The isolation enclosure 14 is impermeable and has a body portion 16, a cap portion 17, and an opening 20 that is selectively sealable by a closure portion 22. In one embodiment, the body portion 16 is a flexible bag constructed of a material that is transparent or translucent. The cap portion 17 is constructed of a rigid material and has an inlet port 18 and an outlet port 19. Of course, one of ordinary skill in the art will recognize that the body portion 16 can be semi-rigid or rigid and the cap portion 17 can be semi-rigid or even flexible in whole or part without detracting from the present invention.

Opening 20 is optionally located in any convenient location on the isolation enclosure 14. In one embodiment, the opening 20 is formed between the body portion 16 and the cap 17. The closure portion 22 includes a fastener 24 located on the body portion 16 and a fitting 26 located on the cap portion 17. The fastener 24 and fitting 26 mate to selectively seal the opening 20 and form the closure portion 22. It will be understood by one of ordinary skill in the art that the closure portion 22 may be of any know design, including but not limited to snaps fittings, threaded fittings, latch fittings, hook fittings, and clamp fittings.

Figure 3:
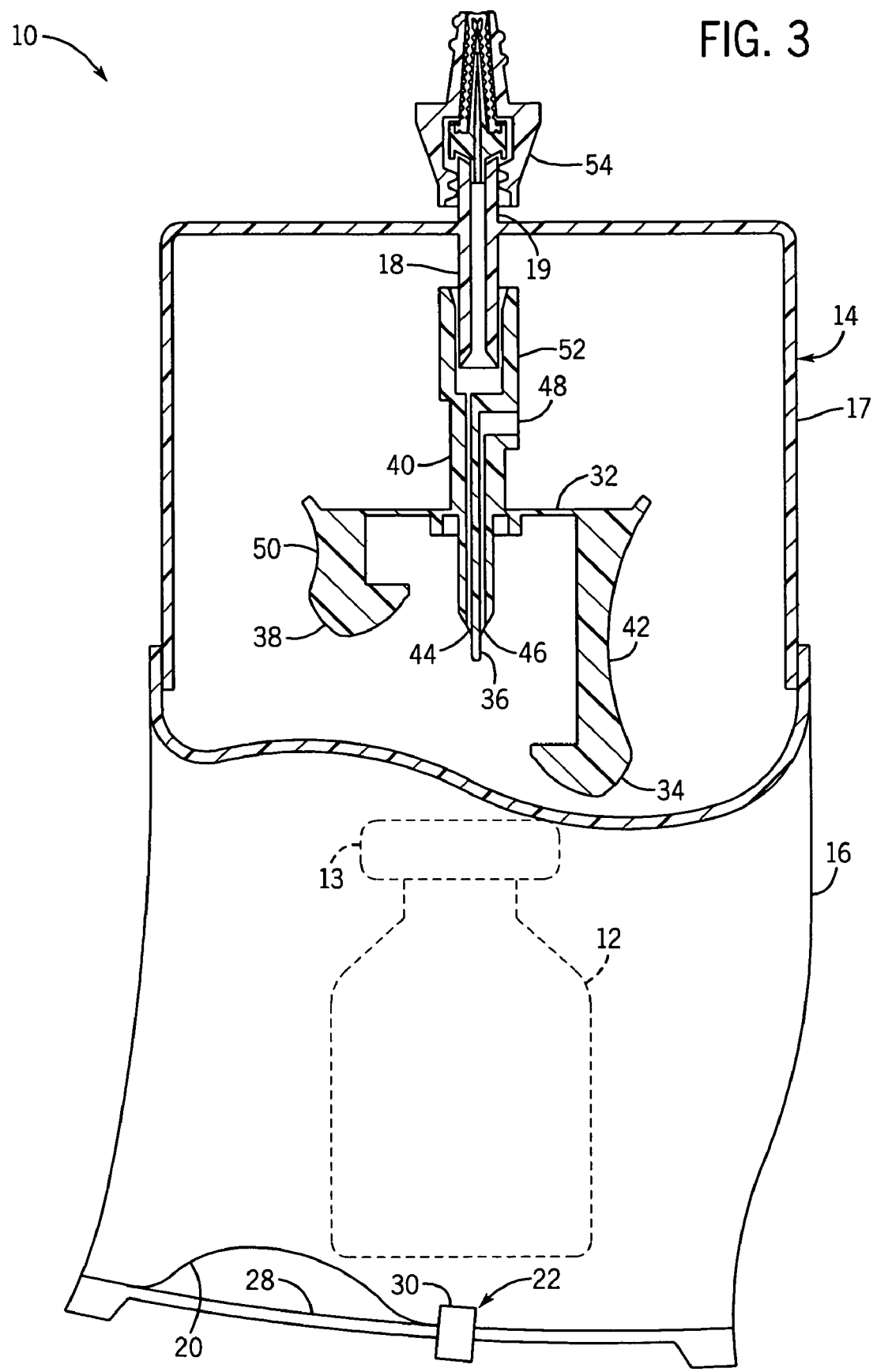
FIG. 3 is a partial sectional side view similar to FIG. 2 of an alternative embodiment of the material handling system of this invention.

With reference to FIG. 3, the opening 20 is formed in the body portion 16 in another embodiment. The closure portion 22 includes a mated track 28 located on the body portion 16 about the opening 20 and a zipper element 30 located on body portion 16 and about the mated track 28. The zipper element 30 is slidably associated with the mated track 28 to selectively close the opening 20. It will be understood by one of ordinary skill in the art that the closure portion 22 may be any know design, including but not limited to clips, clamps, zipper free mated track seals, and adhesive.

A latching extraction element 32 is attached to the cap portion 17 and has a preceding engaging member 34 to secure the vial 12 to the material handling system 10, an extraction member 36 to extend into and remove material from the vial 12, and a primary engaging member 38 to secure the vial 12 to the extraction member 36.

Figure 4:
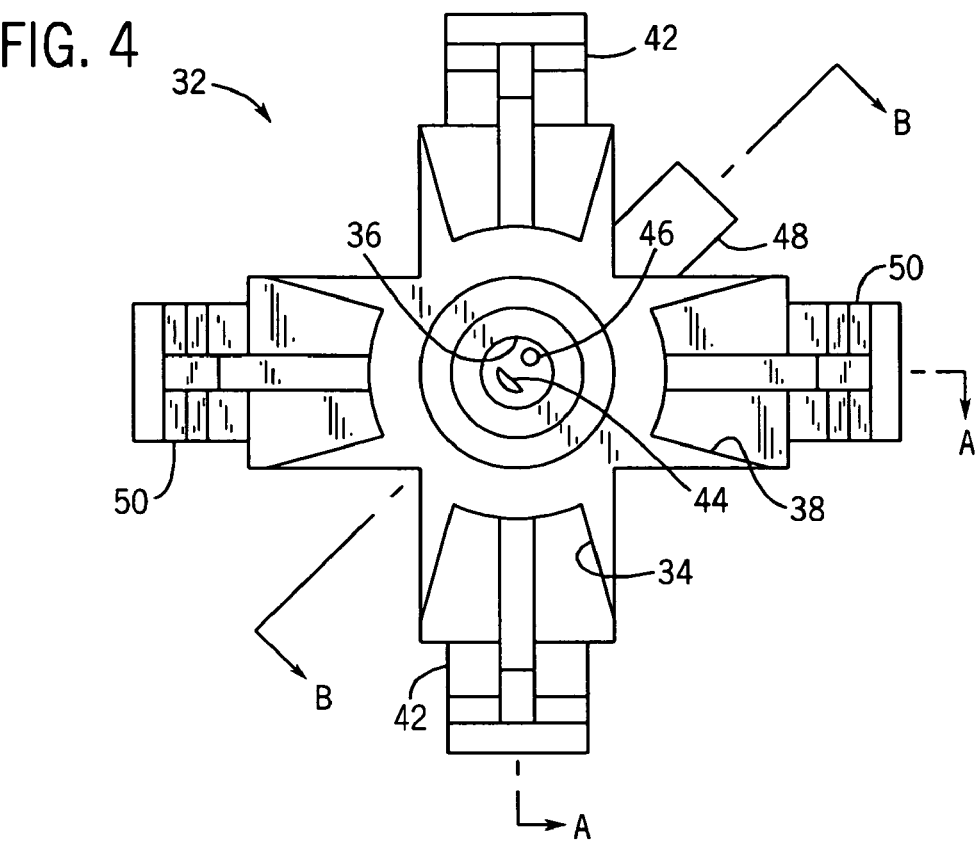
FIG. 4 is a bottom view of a latching extraction element of the present invention.
Figure 8:
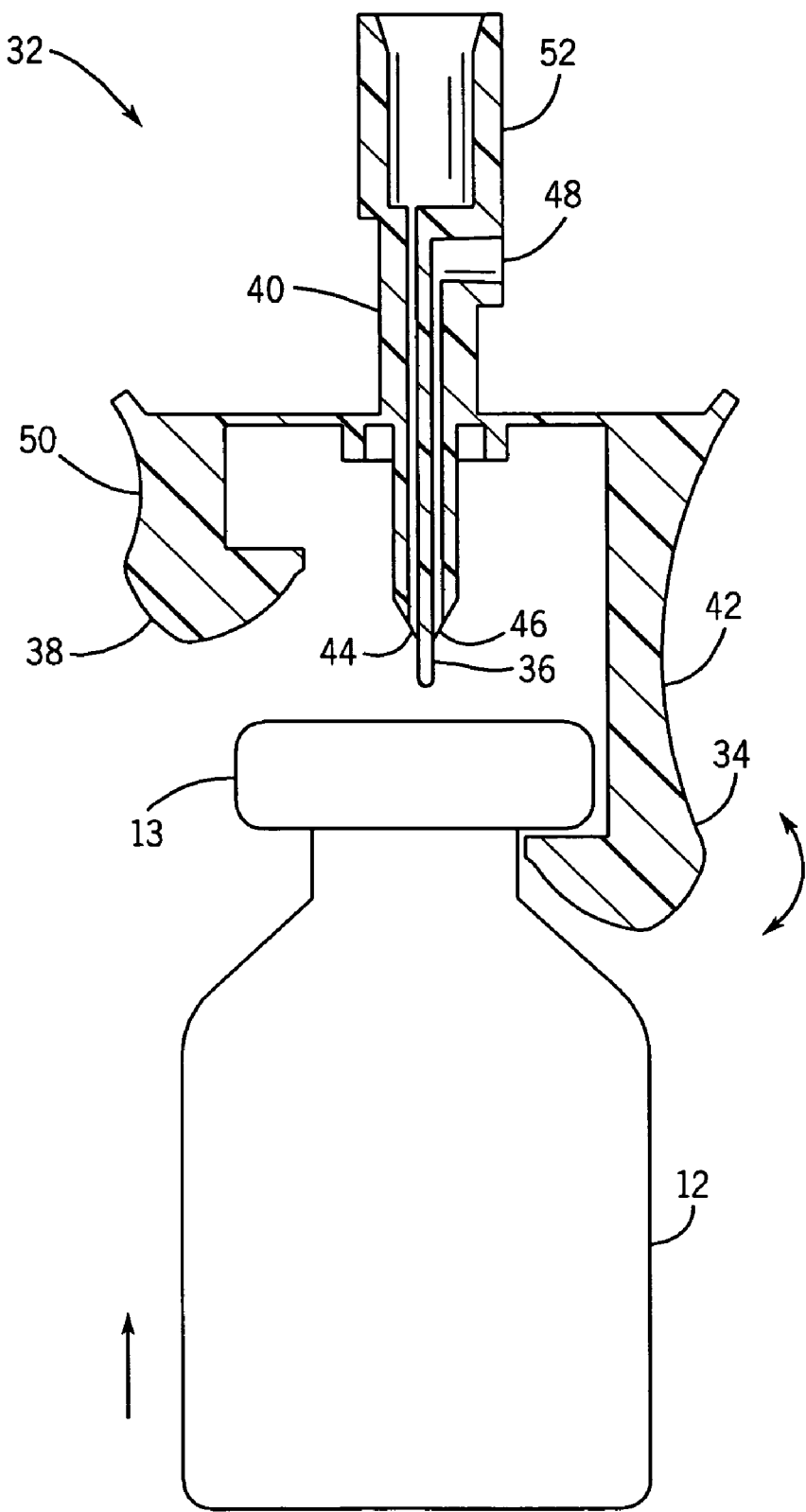

With reference to FIG. 4, the preceding engaging member 34 is mounted on a body portion 40. The preceding engaging member 34 has a plurality of latch arms 42 positioned, preferably equally spaced peripherally, around the body portion 40 and extending from the body portion 40 in the same direction as the extraction member 36. With reference to FIG. 8, the latch arms 42 are positioned and adapted to secure the vial 12 to the extraction member 36 in a first or preceding fixed position wherein the extraction member 36 is outside the vial 13. Once the vial 12 is secured, the opening 20 is closed to seal the isolation enclosure 14.

Figure 9:
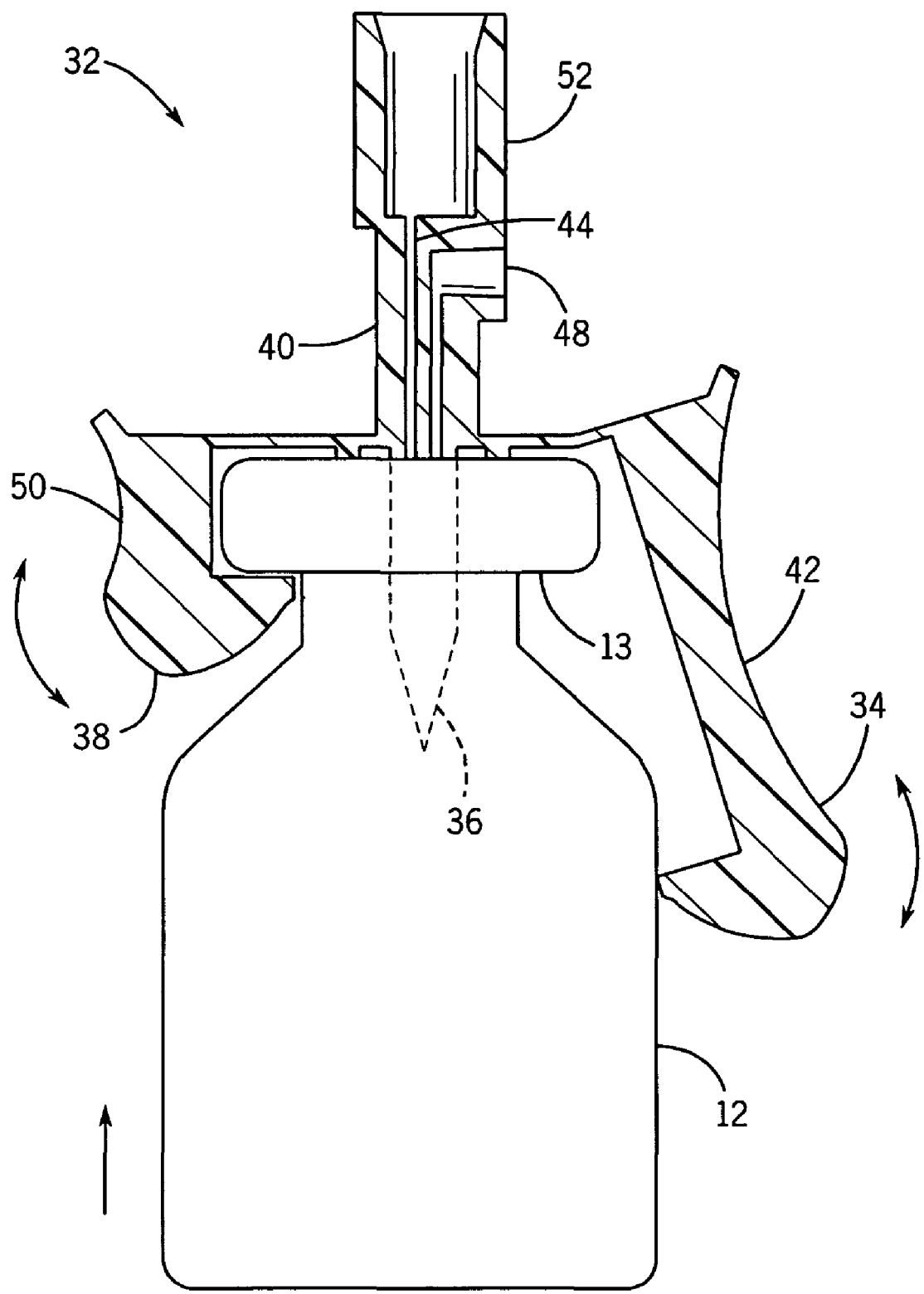
Figure 10:
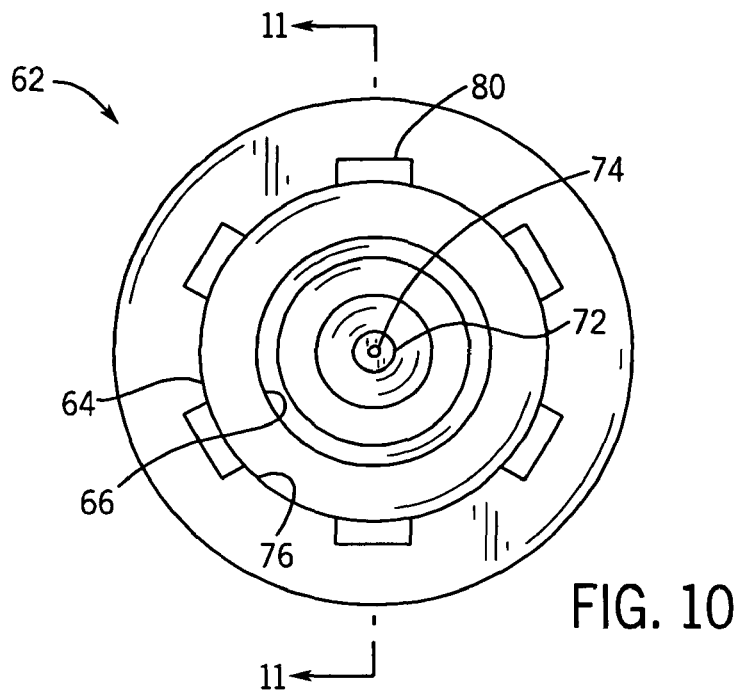
FIG. 10 is a rear view of an adaptor of the present invention.
Figure 11:
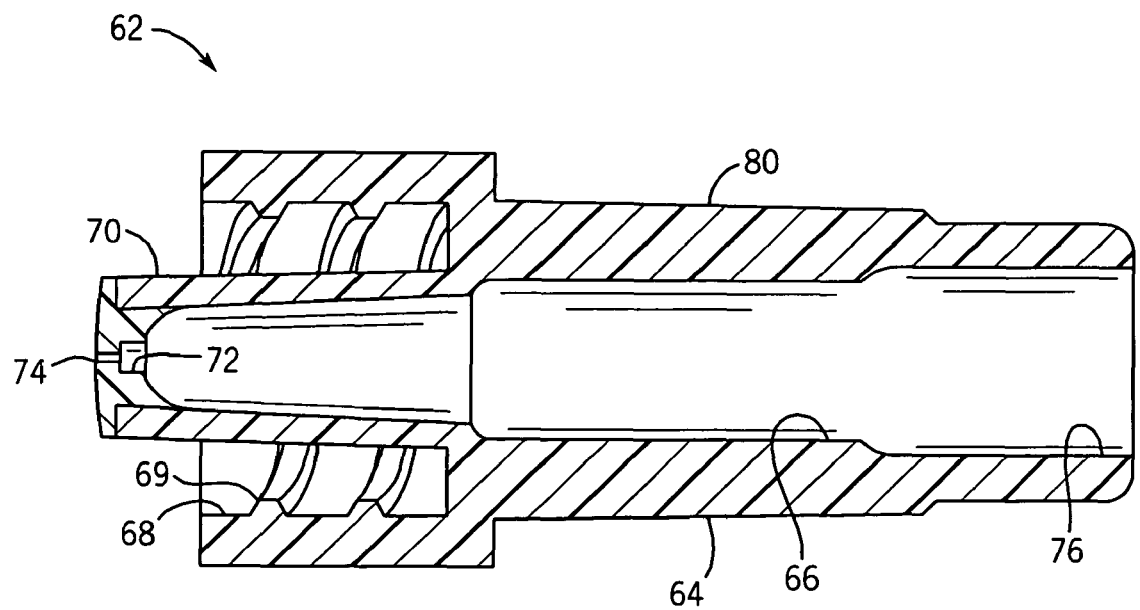
FIG. 11 is a sectional side view of the adaptor of the present invention.

With reference to FIG. 7, the extraction member 36 is located at a proximal end of the body portion 40 and has an elongated fluid passage 44 extending through both the extraction member 36 and the body portion 40. With reference to FIG. 9, the extraction member 36 is adapted to be inserted into the vial 12 (preferably by puncturing the closure 13) and to remove material from the vial 12 through the fluid channel 44. The extraction member 36 can be of any known design other than a needle, including but not limited to a spike or piercing pin, a blunt cannula, and a tube. For example, a spiking pin is illustrated in the figures.

With reference to FIG. 6. a vent channel 46 extends through both the extraction member 36 and the body portion 40, to a vent port 48. The vent channel 46 allows gas in the vial 12 to escape vial the vent port 48 when fluid is inserted into the vial 12 by the fluid channel 44.

Figure 5:
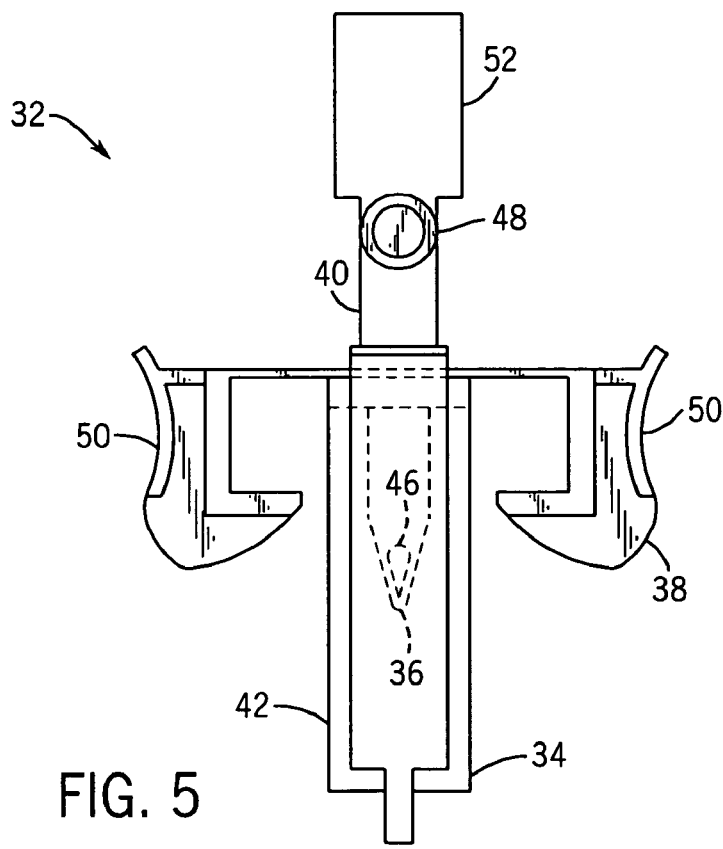
FIG. 5 is a side view of the latching extraction element of the present invention.

With reference to FIGS. 4 and 5, the primary engaging member 38 has a plurality of latch arms 50 positioned, preferably equally spaced peripherally, around the body portion 40 and extending from the body portion 40 in the same direction as the extraction member 36. The latch arms 50 are preferably positioned in staggered relation to the latch arms 42 of the preceding engaging member 34 around the body portion 40. With reference to FIG. 9, the latch arms 50 are positioned and adapted to secure the vial 12 in a second latched or primary fixed position with the extraction member 36 extending thereinto. The extraction member 36 extends a greater distance from the body portion 40 than the latch arms 50, but less than the latch arms 42.

With reference to FIG. 2, a connecting member 52 is located at a distal end of the body portion 40. The connecting member 52 is in fluid communication with the fluid passage 44 and is capable of attaching the latching extraction element 32 to the inlet port 18 of the cap portion 17.

International Publication Number WO 94/08549 describes one embodiment of a latching extraction element or piercing pin suitable for the present invention; said description is expressly incorporated herein in its entirety.

As best seen in FIGS. 2 and 3, a valve 54 is mounted to the outlet port 19 of the cap portion 17, outside the isolation enclosure 14. The valve 54 is in fluid communication with the fluid passage 44 and controls the flow of fluid to and from the vial 12.

With reference to FIGS. 2, 3, 12 and 13, the valve 54 has a threaded outer surface 56, a hollow spiked pin 58 connected in fluid flow communication with the fluid passage 44, and a seal member 60 positioned about the hollow spiked pin 58 to selectively restrict flow through the hollow spiked pin 58.

U.S. Pat. No. 5,738,663 describes one embodiment of a valve suitable for the present invention; said description is expressly incorporated herein in its entirety. The valve described in U.S. Pat. No. 5,738,663 is commonly know as a CLAVE® valve and is commercially available from ICU Medical Inc. of San Clemente, Calif., U.S.A.

With reference to FIGS. 10-13, and adaptor 62 permits flow through valve 54 when coupled to the valve 54 and restricts flow when uncoupled from the valve 54. The adaptor 62 has a body 64 with an elongated fluid passage 66 therethrough. A fastening element 68, which includes raised grips, threads, or lugs 69 thereon, is located at a proximal end of the body 64 for releasably coupling the adaptor 62 to the valve 54 and drawing them together in an axial direction. Such a coupling is commonly called a luer-lock connection.

An actuating post 70 located at the proximal end of the body 64 and along the fluid passage 66. The actuating post 70 extends beyond the fastening element 68 in the proximal direction. The actuating post 70 is adapted to penetrate the valve 54, compress the seal member 60, and expose the hollow spiked pin 58, thus opening the valve 54.

The adaptor 62 has a reseal member 72 coupled to the actuating post 70 and in fluid communication with the fluid passage 66. The reseal member 72 is preferably formed of a resilient elastomeric material and has a preslit opening 74 that is normally closed due to the resiliency of the reseal member 72. The preslit opening 74 is adapted to receive the hollow spiked pin 58, opening the adaptor 62 to fluid flow from the valve 54. The preslit opening 74 closes when uncoupled from the valve 54, thus restricting flow out of the fluid passage 66.

A port 76 is located at a distal end of the body 64 and along the fluid passage 66. The port 76 is adapted to fluidly connect the adaptor 62 to a needless syringe 78. Raised grips, threads or lugs 80 are provided on the body 64 for facilitating connecting the adaptor 62 to the needleless syringe 78. It will be understood to one skilled in the art, that the adaptor 62 and needleless syringe 78 could be made of a unitary construction.

With a reference to FIGS. 2, 8, 9, 12 and 13, in operation the vial 12 is placed within the open isolation enclosure 14. The vial 12 is secured to the material handling system 10 in a first preceding latched or fixed position by forcing the vial 12 to engage the preceding engaging member 34. Once the vial 12 is secured, the isolation enclosure 14 is closed.

Alternatively, the latching extraction element 32 is provided separate from the isolation enclosed 14. In this case, the vial 12 is first secured to the preceding engaging member 34 outside the isolation enclosure 14. Once the latching extraction element 32 and vial 12 are secured together, they are placed within the open isolation enclosure 14. The connecting member 52 of the latching extraction element is then attached to the inlet port 18 of the cap portion 17, securing the vial 12 within the isolation enclosure 14. Once the vial 12 is secured, the isolation enclosure 14 is closed.

The vial 12 can then be safely punctured by gripping the vial through the flexible bag body portion 16 and forcing the vial 12 to simultaneously engage the extraction member 36 and the primary engaging member 38. The extraction member 36 thus punctures the vial 12 and permits access to the vial 12. The primary engaging member 38 secures the vial 12. The primary engaging member 38 secures the vial 12 to the extraction member 36.

Typically, a diluent will be added at this point to the vial 12. To accomplish this, a diluent containing needless syringe 78 is equipped with the adaptor 62. The adaptor 62 is engaged to the valve 54, opening both the hollow spiked pin 58 and the preslit opening 74 to fluid flow. The diluent is added to the vial 12, and excess gas is vented from the vial through vent port 48.

Once diluted, a portion of the vial 12 contents is removed into the syringe 78. The adaptor 62 and syringe 78 are disconnected from the valve 54. When disconnected, the hollow spiked pin 58 and the preslit opening 74 are resealed, maintaining their respective contents in isolation. At this point the vial 12 remains pierced by the extraction member 36 and fixed by the primary engaging member 38.

The contents of the syringe 78 are now transferred to a desired destination. The transfer occurs by removably associating the adaptor 62 and syringe 78 to a second valve 54 located remotely from the isolation enclosure 14. Again, both the hollow spiked pin 58 and the preslit opening 74 are opened allowing fluid to pass into the second valve 54.

It is therefore seen that the present invention provides a method and means capable of securing a vial within an impermeable isolation enclosure. The present invention further provides a method and means capable of piercing a vial within the impermeable isolation enclosure in a fixed position; and selectively accessing the contents of the vial. The present invention also provides a method and means capable of safely transferring a portion of the vial contents, while the vial remains pierced within an impermeable isolation enclosure.

It is therefore seen that this invention will accomplish at least all of its stated objectives.

We claim:

1. A method of accessing materials from a sealed vial, comprising:
    providing a latching extraction element comprising a body portion, an extraction member on the body portion adapted to be inserted into the vial, a preceding engaging member mounted the body portion, and a primary engaging member mounted on the body portion to secure the vial to the extraction member, the preceding engaging member including a plurality of latch arms extending from the body portion in a direction common with the extraction member, the primary engaging member including a plurality of latch arms extending from the body portion in the common direction, the latch arms of the preceding engaging member extending a greater distance from the body portion in the common direction than the latch arms of the primary engaging member;
    placing the vial into an impermeable isolation enclosure through a selectively sealable opening thereof;
    securing the vial in a preceding fixed position in which the vial is secured to the latching extraction element but the extraction member is outside the vial by forcing the vial between and into engagement with the latch arms of the preceding engaging member;
    mounting the latching extraction element within and to the impermeable isolation enclosure;
    sealing closed the selectively sealable opening of the impermeable isolation enclosure;
    securing the vial to the latching extraction element in a primary fixed position by forcing the vial into engagement between the latch arms of the primary engaging member such that the extraction member pierces the vial;
    selectively accessing the contents of the vial externally from the closed impermeable isolation enclosure via a normally closed valve mounted to and outside of the impermeable isolation enclosure and in fluid communication with the extraction member of the latching extraction element;
    removing at least a portion of the contents of the vial through the valve and into a needleless syringe;
    transferring removed portion in isolation and maintaining a remaining portion of the contents in isolation within the vial while the vial remains pierced by the extraction member and in the primary fixed position; and
    adding a diluent to the vial via the valve while the vial is pierced and in the primary fixed position and the impermeable isolation enclosure is closed;
    wherein the step of adding the diluent includes venting gas from the vial through a vent channel extending through both the extraction member and the body portion to a vent port within the closed impermeable isolation enclosure.

2. The method of claim 1, wherein the latching extraction element is provided separate from the impermeable isolation enclosure and the step of securing the vial in the preceding fixed position is completed prior to the step of placing the vial into the impermeable isolation enclosure.

3. The method of claim 1, wherein the step of mounting the latching extraction element to the impermeable isolation enclosure comprises attaching the latching extraction element to an inlet port of a cap portion of the impermeable isolation enclosure.

4. The method of claim 1, wherein the step of adding a diluent comprises the substeps of:
    removably coupling a first end of an adaptor to a diluent-containing needleless syringe while a second end of the adaptor remains sealed by a normally closed reseal member so as to restrict diluent from leaking from the syringe; and
    then removably coupling the second end of the adaptor to the valve on the impermeable isolation enclosure so that the reseal member of the adaptor and the valve are opened to fluid flow.

5. The method of claim 1, wherein the step of mounting the latching extraction element to the impermeable isolation enclosure is completed prior to placing the vial into the impermeable isolation enclosure.

6. The method of claim 1, wherein the step of securing the vial in the preceding fixed position includes engaging a necked portion of the vial with the latch arms of the preceding engaging member.

7. The method of claim 6, wherein the step of securing the vial in the primary fixed position includes forcing the vial beyond the latch arms of the preceding engaging member and toward the extraction member such that the latch arms of the primary engaging member engage a necked portion of the vial.

8. The method of claim 1, wherein the step of securing the vial to the latching extraction element in the primary fixed position is accomplished by gripping the vial through a flexible portion of the impermeable isolation enclosure.

9. The method of claim 1, wherein the step of transferring the removed portion in isolation includes the substeps of:

uncoupling the second end of the adaptor from the valve so as to restrict fluid flow from both the valve and the adaptor;

moving the syringe to a desired destination for delivery of the removed portion; and removably coupling the second end of the adaptor to a second normally closed valve that is remote from the impermeable isolation enclosure.

* * * * *